United States Patent [19]
Szabo et al.

[11] 3,993,065
[45] Nov. 23, 1976

[54] FLUID INFUSION APPARATUS

[76] Inventors: Anthony W. Szabo, 37 Cobblewood Road, Livingston, N.J. 07039; Louis R. M. Del Guercio, 14 Pryor Lane, Larchmont, N.Y. 10538

[22] Filed: May 20, 1975

[21] Appl. No.: 579,232

[52] U.S. Cl. .......................... 128/218 A; 128/214 F; 128/DIG. 12; 222/175
[51] Int. Cl.² ........................................... A61M 5/00
[58] Field of Search ........ 128/218 A, 218 R, 218 F, 128/214 F, 215, DIG. 12, DIG. 13, 2 R; 222/386, 390, 391, 309, 175

[56] References Cited
UNITED STATES PATENTS

| | | | |
|---|---|---|---|
| 1,751,139 | 3/1930 | Feinstein | 128/218 A |
| 2,703,084 | 3/1955 | Tomlinson | 128/214 F |
| 2,925,814 | 2/1960 | Vibber et al. | 128/214 F |
| 3,464,359 | 9/1969 | King et al. | 128/214 F X |
| 3,720,211 | 3/1973 | Kyrias | 128/218 A |
| 3,799,406 | 3/1974 | St. John et al. | 128/218 A X |

*Primary Examiner*—John D. Yasko
*Attorney, Agent, or Firm*—Larson, Taylor and Hinds

[57] ABSTRACT

An improved fluid infusion apparatus is presented of the type having a power means and a syringe connected therewith. The syringe is comprised, in part, of a piston and a cylindrical body. The improvement comprises a flexible connecting member for connecting the piston of the syringe to the power means, thereby permitting the syringe to be responsive to the power means, even when the two are not coaxially aligned, for the administration of a predetermined amount of fluid at a predetermined rate.

6 Claims, 2 Drawing Figures

FLUID INFUSION APPARATUS

BACKGROUND OF THE INVENTION

1. Field of the Invention

This invention relates to fluid infusion devices and, more particularly, to automatic infusion devices which are highly adaptable to the contours of a patient's body.

2. Description of the Prior Art

Prior art infusion devices can be divided into two categories, those which are portably mountable to an ambulatory patient, and those which are not mountable and require the patient to be confined to a bed or chair. The design of the portably mountable devices usually leaves much to be desired. Even though the devices allow the patient to be ambulatory, their designs usually cannot conveniently be made to conform to the contours of the patient's body. An example of portably mountable devices are disclosed in U.S. Pat. No. 3,415,419 issued to Jewett and in copending application 408,264 by Szabo and Del Guercio, Szabo and Del Guercio also being the inventors of the present invention.

Nonmountable devices are disclosed in U.S. Pat. Nos. 2,498,672 issued to Glass and 3,701,345 issued to Heilman, and also include the standard gravity bed bottle systems. These mountable devices also suffer from the adaptability disadvantage of the portably mountable devices. They further suffer from the disadvantage of restricting the movement of the patient to whom they are connected.

SUMMARY OF THE INVENTION

The present invention provides for an improved fluid infusion device that is highly adaptable to the shape of a patient's body.

In accordance with a preferred embodiment of the invention, an improved fluid infusion apparatus of the type having a power mechanism and a syringe connected therewith is provided. The syringe comprises in part a piston and a cylindrical body, and is for administering a predetermined amount of fluid at a predetermined rate over an extended time period. The improvement of the infusion device comprises a flexible connecting member for connecting the syringe to the power mechanism thereby causing the piston of the syringe to be responsive to the power means, even when the two are not coaxially aligned.

Additional features and advantages of the invention will be set forth in, or apparent from, the detailed description of preferred embodiments of the invention found hereinbelow.

DETAILED DESCRIPTION OF THE PREFERRED EMBODIMENTS

Figure 1:
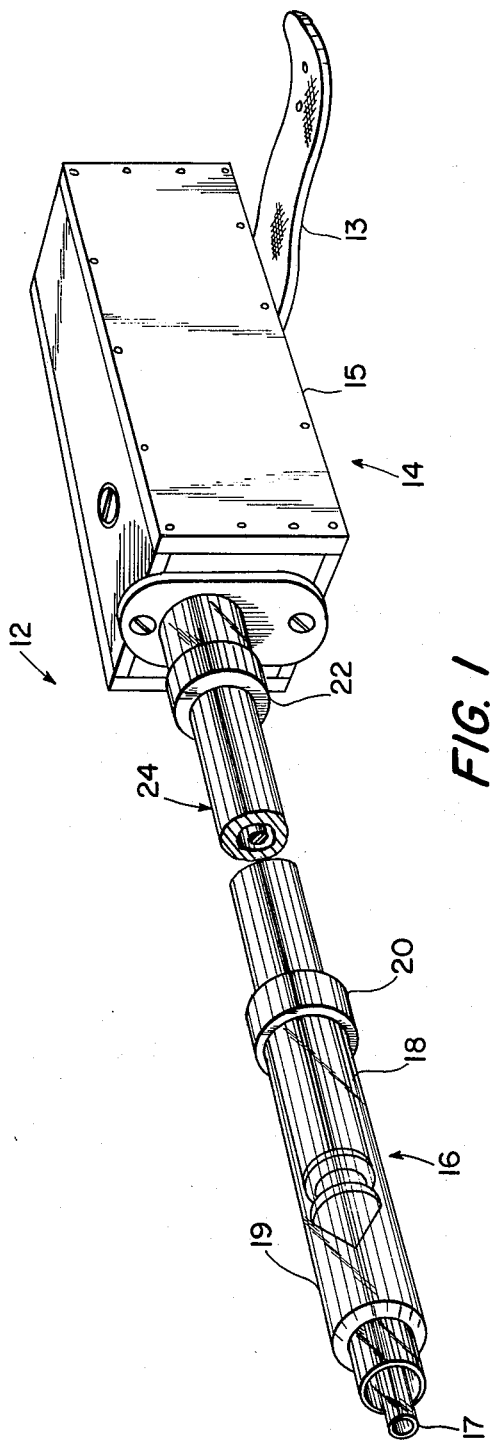
FIG. 1 is a perspective view of a presently preferred embodiment of the invention with parts thereof cut away.

With reference to FIG. 1, a presently preferred embodiment of an improvement for a fluid infusion apparatus 12 is shown in accordance with the invention. The improved apparatus 12 is depicted in one possible configuration whereby an infusion power and timing mechanism 14 is removably connected to a syringe 16. The particular power and timing mechanism 14 depicted has a strap 13, by which the aforesaid is portably attachable to a patient's body, and a housing 15. This particular mechanism 14 is described in copending application number 408,264 filed by Szabo and Del Guercio. It should be understood, however, that a variety of power and timing mechanisms can be used. In general, mechanism 14 comprises a mechanical or electrical power source. The mechanical power source can include, for example, a spring mechanism, while the electrical power source can include an electric motor. The desired power source is in turn regulated by a mechanical or an electrical timing device such as a clock.

Syringe 16 is a well known device and includes a dispensing end 17, a cylindrical body 19 and a plunger 18, coaxially mounted therein. Syringe 16 is made of plastic or glass and can be disposably or reusable. Fluid is stored in cylindrical body 19. In order to fill or empty body 19, plunger 18 is longitudinally pushed into or pulled out from body 19. This creates a suction or pressure which draws fluid into or pushes it out of dispensing end 17 of syringe 16.

As can best be seen in FIG. 1, apparatus 12 further comprises two end connections 20 and 22 and a flexible connecting member 24. End connector 20 removably connects flexible member 24 to syringe 16 and end connector 22 removably connects flexible member 24 to housing 15 of power and timing mechanism 14. Consequently, a malfunctioning or contaminated syringe 16, or a malfunctioning power and timing mechanism 14 can easily be replaced.

End connectors 20 and 22 are preferably either U-shaped clips that are slid tangentially into position with connecting member 24, or clips that are slid coaxially into position. End connectors 20 and 22 are preferably made of a flexible metalic or a tough plastic material.

Figure 2:
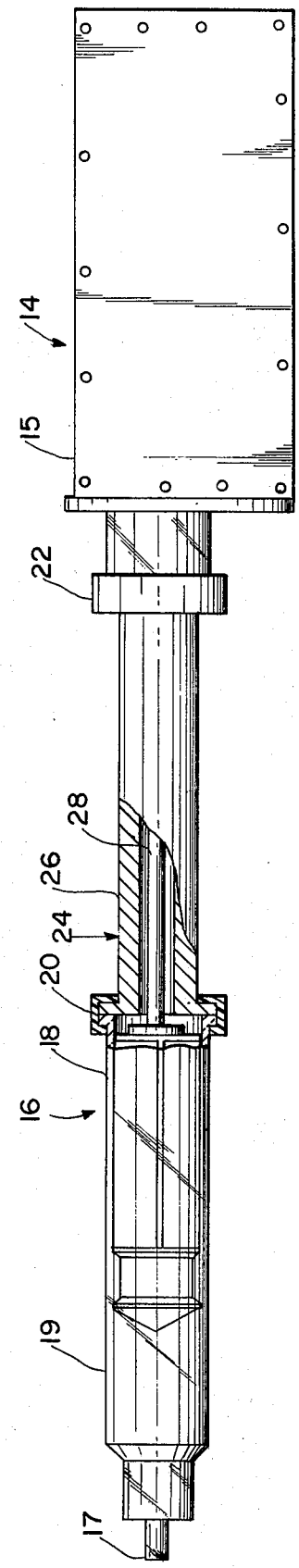
FIG. 2 is a front elevation view of the invention presented in FIG. 1, with parts thereof cut away.

With reference to FIG. 2, flexible connecting member 24 is comprised of a flexible outer casing 26 and a flexible rod 28 slidably coaxially mounted therein. Flexible outer casing 26 is preferably comprised of a flexible rubber, plastic or metal tube. Flexible rod 28 is preferably comprised of a flexible plastic or metal rod.

The end of flexible casing 26 proximal to connector 20 abuts cylindrical body 10 of syringe 16 and is removably held in this position by connector 20. The end of flexible casing 26 proximal to connector 22 abuts housing 15 of timing and power mechanism 14 and is removably held in this position by connector 22. Flexible casing 26 thus is the supporting member by which syringe 16 is held to housing 15 of power and timing mechanism 14. Further since flexible casing 26 encases flexible rod 28, it provides support and protection from fouling thereto.

The end of flexible rod 28 proximal to connector 20 is removably connected to plunger 18 of syringe 16. The end of flexible rod 28 proximal to connector 22 is removably connected to power and timing mechanism 14. Consequently, owing to flexible connecting member 24 power and timing mechanism 14 can operate plunger 18 even when it is out of coaxial allignment therewith. Thus, mechanism 14 can push plunger 18 longitudinally into syringe 16 at a desired rate, thereby dispensing fluid therefrom at a desired rate.

Apparatus 12 in use with a portable infusion device as depicted in FIG. 1 allows greater flexibility in the location of power and timing mechanism 14. Mechanism 14 can, for example, be placed on the upper arm while syringe 16 is placed on the lower arm without the need to immobolize the entire arm of a patient. Thus, syringe 16 can truely be placed at the desired location of infusion of fluid into the patient's body and is no longer restrained by a rigid connection to mechanism 14.

Improvement 12 can also be used with a nonportable infusion device such as the device depicted in FIG. 1 of U.S. Pat. No. 2,498,672 issued to Glass. Used in this manner, improvement 12 also allows syringe 16 to be placed on the patient at the desired infusion location.

Although the invention has been described with respect to an exemplary embodiment thereof, it will be understood by those of ordinary skill in the art that variations and modifications may be effected within the scope and spirit of the invention.

I claim:

1. An improved fluid infusion apparatus for an ambulatory patient of the type having a portable power and timing means mountable to the patient and received in a housing and a syringe operable thereby, said syringe comprising in part a piston, received in a cylindrical body, said apparatus for administering a predetermined amount of fluid at a predetermined rate over an extended time period, wherein the improvement comprises a flexible connecting member connecting said syringe to said power means for causing said piston of said syringe to be responsive to said power and timing means and means attached to said housing for securement to a patient.

2. An apparatus in accordance with claim 1 wherein said power timing means includes a housing therefor wherein said flexible connecting member includes an elongated flexible rod and an elongated flexible casing concentrically surrounding said flexible rod, said apparatus further comprising means for removably attaching said elongated flexible casing to said syringe and to said housing of said power and timing means.

3. An apparatus in accordance with claim 2 wherein said means comprises removable connecting clips that are coaxially and slidably mounted on said flexible casing, one of said clips for sliding into engagement with said syringe so as to connect said syringe to said casing, and one of said clips for sliding into engagement with said housing so as to connect said housing to said casing.

4. An apparatus in accordance with claim 1 wherein said flexible member comprises an elongated flexible rod which connects said piston to said power and timing means.

5. An apparatus in accordance with claim 4 wherein said flexible member further comprises an elongated flexible casing concentrically surrounding said flexible rod connecting said housing of said power and timing means to said cylindrical body of said syringe, and for permitting longitudinal movement therein of said flexible rod relative to said housing and said cylindrical body of said syringe.

6. An apparatus in accordance with claim 5 further including removable connecting clips that are coaxially and slidably mounted on said flexible casing, one of said clips for sliding into engagement with said body of said syringe so as to connect said syringe to said casing, and one of said clips for sliding into engagement with said housing so as to connect said housing to said casing.

* * * * *